United States Patent

King

[11] 4,165,976
[45] Aug. 28, 1979

[54] SYNERGISTIC HERBICIDAL COMPOSITIONS

[75] Inventor: David L. King, Los Gatos, Calif.

[73] Assignee: Stauffer Chemical Company, Westport, Conn.

[21] Appl. No.: 898,363

[22] Filed: Apr. 21, 1978

[51] Int. Cl.² .............................................. A01N 9/22
[52] U.S. Cl. .......................................... 71/88; 71/94; 71/95; 71/100
[58] Field of Search ......................... 71/100, 88, 94, 95

[56] References Cited

U.S. PATENT DOCUMENTS 3,198,786  8/1965  Tilles et al. .......................... 71/100 X

*Primary Examiner*—Joseph Paul Brust
*Attorney, Agent, or Firm*—M. Henry Heines

[57] ABSTRACT

Synergistic herbicidal activity is displayed by compositions comprising the following two components:
(a) an anilide of the formula

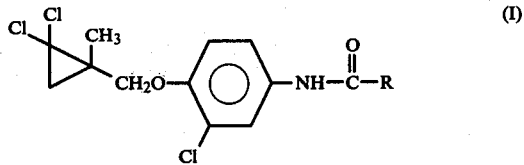

(I)

in which R is a member selected from the group consisting of $C_1$–$C_{10}$ alkyl, $C_2$–$C_4$ alkenyl, and $C_3$–$C_5$ cycloalkyl; and
(b) a thiocarbamate of the formula

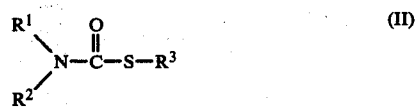

(II)

in which $R^1$ and $R^2$ are independently $C_1$–$C_4$ alkyl, or $R^1$ and $R^2$ conjointly form $C_2$–$C_7$ alkylene; and $R^3$ is $C_1$–$C_4$ alkyl, in a weight ratio of anilide to thiocarbamate of 0.001–50:1.

8 Claims, No Drawings

SYNERGISTIC HERBICIDAL COMPOSITIONS

DESCRIPTION OF THE INVENTION

This invention relates to synergistic herbicidal compositions.

It has been discovered that synergism in the control of undesired vegetation is exhibited by compositions comprising the following two components:

(a) an anilide of the formula

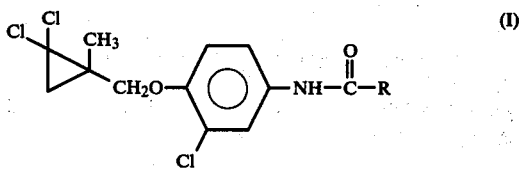

in which R is a member selected from the group consisting of $C_1$-$C_{10}$ alkyl, $C_2$-$C_4$ alkenyl, and $C_3$-$C_5$ cycloalkyl; and (b) a thiocarbamate of the formula

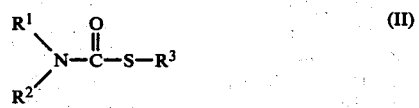

in which $R^1$ and $R^2$ are independently $C_1$-$C_4$ alkyl, or $R^1$ and $R^2$ conjointly form $C_2$-$C_7$ alkylene; and $R^3$ is $C_1$-$C_4$ alkyl, in a weight ratio of anilide to thiocarbamate of 0.001-50:1.

Within the scope of the above-defined general formulae, certain embodiments are preferred, as indicated below:

In Formula I, R is preferably a member selected from the group consisting of $C_2$-$C_4$ alkenyl and $C_3$-$C_5$ cycloalkyl.

In Formula II, $R^1$ and $R^2$ preferably conjointly form $C_2$-$C_7$ alkylene, and more preferably $C_4$-$C_7$ alkylene.

The terms "alkyl" and "alkylene" as used herein are intended to include both straight- and branched-chain groups. All carbon atom ranges are intended to be inclusive of both upper and lower limits.

The term "herbicide", as used herein, means a compound which controls or modifies the growth of plants. By the term "herbicidally effective amount" is meant an amount of compound which causes a modifying effect upon the growth of plants. By "plants" is meant germinating seeds, emerging seedlings and established vegetation, including roots and above ground portions. Such modifying effects include all deviations from natural development, for example, killing, retardation, defoliation, desiccation, regulation, stunting, tillering, stimulation, leaf burn, dwarfing and the like. The compositions of the present invention are particularly effective in controlling weeds in flooded rice paddies.

The term "synergism" is employed in its traditional sense and describes a herbicidal effect of a composition containing two or more active herbicidal compounds which is greater than the sum of the herbicidal effects of the individual compounds when used alone.

The anilides of the present compositions can be prepared by the procedures described in commonly assigned co-pending application Ser. No. 807,940, filed June 21, 1977. Examples of such anilides are:

3-chloro-4-(2,2-dichloro-1-methyl-cyclopropyl) methoxy crotonyl anilide 3-chloro-4-(2,2-dichloro-1-methyl cyclopropyl) methoxy methacrylyl anilide 3-chloro-4-(2,2-dichloro-1-methyl cyclopropyl) methoxy cyclopropane carboxylic acid anilide 3-chloro-4-(2,2-dichloro-1-methyl cyclopropyl) methoxy propionyl anilide 3-chloro-4-(2,2-dichloro-1-methyl cyclopropyl) methoxy iso butyryl anilide 3-chloro-4-(2,2-dichloro-1-methyl cyclopropyl) methoxy butyryl anilide 3-chloro-4-(2,2-dichloro-1-methyl cyclopropyl) methoxy 2'-methyl butyryl anilide 3-chloro-4-(2,2-dichloro-1-methyl cyclopropyl) methoxy 2',2'-dimethyl valeryl anilide The thiocarbamates of the present compositions are well known herbicides and can be prepared by the procedures described in U.S. Pat. No. 3,198,786. Examples of such thiocarbamates are:

S-ethyl hexahydro-1H-azepine-1-carbothioate
S-ethyl di-n-propylthiocarbamate
S-ethyl diisobutylthiocarbamate
S-n-propyl di-n-propylthiocarbamate
S-n-propyl n-butylethylthiocarbamate.

The anilide and thiocarbamate herbicides are used in a weight ratio of anilide to thiocarbamate of 0.001-50:1, preferably 0.01-10:1, and most preferably 0.1-8:1.

Application rates will depend upon the weeds to be controlled and the degree of control desired. In general, the compositions of this invention are most efficiently employed at a rate of 0.01 to 50 pounds per acre (0.011 to 56 kilograms per hectare), preferably 0.1 to 25 pounds per acre (0.011 to 28 kilograms per hectare).

Herbicidal compositions illustrative of those embodied in the instant application were prepared and synergistic effect evaluated in the following examples.

EXAMPLES

The compositions of the present invention were tested for herbicidal activity and synergism by a postflood-postemergence test in a simulated rice paddy as follows:

Plastic tubs measuring 10×7.5×5.75 inches (25.4×19.0×14.6 centimeters) were filled to a depth of 2 inches (5.1 centimeters) with 8 pounds (3.6 kilograms) of a loamy sand soil, containing 50 parts per million (ppm) each of cis-N[(trichloromethyl)thio]-4-cyclohexene-1,2-dicarboximide (a commercial fungicide designated as Captan ®) and 18-18-18 fertilizer (containing 18% N, 18% $P_2O_5$, and 18% $K_2O$ on a weight basis). One pint (0.47 liter) of the soil was removed, the remaining soil was leveled and seven rows were impressed across the width of the flat. Yellow nutsedge tubers (*Cyperus esculentus*), and seeds of annual morning glory (*Ipomoea purpurea*), curly dock (*Rumex crispus*), sesbania (Sesbania spp.) and rice (*Oryza sativa*) were planted in separate rows. The pint of soil was then used to place a 0.5 inch (1.27 centimeter) layer over the seeds and tubers. The planted soil was placed in a greenhouse, and irrigated by sprinkling as needed to keep the soil moist. Three days after the initial seeding another row was impressed 0.5 inches (1.27 centimeters) deep across the width of the flat and seeds of watergrass (*Echino-* chloa crusgalli) were planted and covered by pinching together the soil on either side of the seeder row. Seven to ten days after the original seeding, the soil was flooded with 2 inches (5.1 centimeters) of water. At flooding time the grass species were in the two leaf stage 1 to 2 inches (2.54 to 5.1 centimeters) high and the nutsedge was 1 inch (2.54 centimeters) high.

Test compounds or combinations were then applied by pipeting into the flood water a prescribed volume of stock solution to produce the desired application rate in pounds of active ingredient per acre (lb/A) or its equivalent in kilograms per hectare. For the particular tubs used, 5.5 milligrams (mg) of active ingredient per tub is equivalent to 1.0 lb/A. The anilide stock solution for an application rate of 1.0 lb/A consisted of 22 mg of the anilide dissolved in 20 milliliters (ml) of acetone containing 1% "Tween 20®" (a commercial emulsifying agent defined as a polyoxyethylene sorbitan monolaurate). The thiocarbamate stock solution for an application rate of 1.0 lb/A was prepared by dissolving 31 mg of an emulsifiable concentrate of the thiocarbamate in 20 ml of water. The emulsifiable concentrate was comprised of 71.3% thiocarbamate. The prescribed pipet volume was 5.0 ml. Stock solutions for other application rates were made with proportional amounts of the anilide or thiocarbamate. Combinations were achieved by pipeting 5.0 ml from each of the appropriately selected stock solutions.

The tubs were allowed to stand for three weeks after the application of the test compounds and water was added as needed to maintain the water level. At the end of three weeks, the species were rated visually as percent control from 0 to 100%, where 0% represents no injury and 100% represents complete kill when compared to an untreated check tub. The percent control was based on the total injury to the plants due to all factors.

The anilides tested were 3-chloro-4-(2,2-dichloro-1-methyl cyclopropyl)methoxy methacrylyl anilide (Table 1) and 3-chloro-4-(2,2-dichloro-1-methyl cyclopropyl)methoxy cyclopropane carboxylic acid anilide (Table 2) in combination with the thiocarbamate S-ethyl hexahydro-1H-azepine-1-carbothioate (OR-DRAM®).

The results of each test are reported in Tables 1 and 2 in the columns headed by the symbol "O" (indicating observed results). These results were then compared with the expected results, shown in the columns headed by the symbol "E", derived from Limpel's formula (Limpel et al., 1962, "Weed Control by Dimethylchloroterephthalate Alone and in Certain Combinations," *Proc. NEWCC*, Vol. 16, pp. 48–53):

$$E = X + Y - (XY/100)$$

where
- $X$ = observed percent injury when one of the herbicides is used alone, and
- $Y$ = observed percent injury when the other herbicide is used alone.

The relationship between the observed result and the expected result for each combination tested is indicated in the columns headed by the symbol "R". When the observed result exceeds the expected result, synergism has been shown, which is represented by the symbol "S". When the observed result is less than the expected result, there is antagonism between the herbicides, represented by the symbol "A". When the observed result equals the expected result, the relationship of the herbicides in the combination is merely additive, as represented by the symbol "Ad."

Table 1

Postflood Test Results - Percent Control

| lb/A Thiocarbamate | lb/A Anilide | Watergrass | | | Yellow Nutsedge | | | Sesbania | | | Annual Morning Glory | | | Curly Dock | | |
|---|---|---|---|---|---|---|---|---|---|---|---|---|---|---|---|---|
| | | O | E | R | O | E | R | O | E | R | O | E | R | O | E | R |
| 1/2 | — | 0 | | | 0 | | | 0 | | | 0 | | | 0 | | |
| 1 | — | 30 | | | 0 | | | 0 | | | 0 | | | 0 | | |
| 2 | — | 50 | | | 0 | | | 0 | | | 0 | | | 0 | | |
| — | 1/16 | 0 | | | 0 | | | 0 | | | 0 | | | 0 | | |
| — | 1/8 | 20 | | | 0 | | | 0 | | | 0 | | | 40 | | |
| — | 1/4 | 80 | | | 0 | | | 0 | | | 60 | | | 60 | | |
| — | 1/2 | 98 | | | 0 | | | 70 | | | 80 | | | 98 | | |
| 1/2 | 1/16 | 10 | 0 | S | 0 | 0 | — | 0 | 0 | — | 0 | 0 | — | 0 | 0 | — |
| 1/2 | 1/8 | 30 | 20 | S | 0 | 0 | — | 20 | 0 | S | 60 | 0 | S | 50 | 40 | S |
| 1/2 | 1/4 | 75 | 80 | A | 0 | 0 | — | 10 | 0 | S | 70 | 60 | S | 80 | 60 | S |
| 1/2 | 1/2 | | | * | — | 0 | — | 80 | 70 | S | 90 | 80 | S | 100 | 98 | S |
| 1 | 1/16 | 20 | 30 | A | 0 | 0 | — | 0 | 0 | — | 60 | 0 | S | 30 | 0 | S |
| 1 | 1/8 | 40 | 44 | A | 0 | 0 | — | 0 | 0 | — | 30 | 0 | S | 60 | 40 | S |
| 1 | 1/4 | 85 | 86 | A | 0 | 0 | — | 0 | 0 | — | 60 | 60 | Ad | 80 | 60 | S |
| 1 | 1/2 | | | * | 50 | 0 | S | 40 | 70 | A | 80 | 80 | Ad | | | * |
| 2 | 1/16 | 70 | 50 | S | 40 | 0 | S | 0 | 0 | — | 0 | 0 | — | 30 | 0 | S |
| 2 | 1/8 | 60 | 60 | Ad | 70 | 0 | S | 20 | 0 | S | 60 | 0 | S | 60 | 40 | S |
| 2 | 1/4 | 85 | 90 | A | 20 | 0 | S | 70 | 0 | S | 80 | 60 | S | 80 | 60 | S |
| 2 | 1/2 | | | * | 60 | 0 | S | 70 | 70 | Ad | 98 | 80 | S | 100 | 98 | S |

*Observed and expected results were too close to 100% for synergism evaluation.

TABLE 2

Postflood Test Results - Percent Control

| lb/A Thiocarbamate | lb/A Anilide | Watergrass | | | Yellow Nutsedge | | | Sesbania | | | Annual Morning Glory | | | Curly Dock | | |
|---|---|---|---|---|---|---|---|---|---|---|---|---|---|---|---|---|
| | | O | E | R | O | E | R | O | E | R | O | E | R | O | E | R |
| 1/2 | — | 0 | | | 0 | 0 | | 0 | | | 0 | | | | | |
| 1 | — | 60 | | | 10 | | | 0 | | | 0 | | | | | |
| — | 1/16 | 0 | | | 0 | | | 60 | | | 40 | | | | | |

TABLE 2-continued

Postflood Test Results - Percent Control

| lb/A Thiocarbamate | lb/A Anilide | Watergrass 0 | Watergrass E | Watergrass R | Yellow Nutsedge 0 | Yellow Nutsedge E | Yellow Nutsedge R | Sesbania 0 | Sesbania E | Sesbania R | Annual Morning Glory 0 | Annual Morning Glory E | Annual Morning Glory R | Curly Dock 0 | Curly Dock E | Curly Dock R |
|---|---|---|---|---|---|---|---|---|---|---|---|---|---|---|---|---|
| — | 1/8 | 0 | | | 0 | | | 100 | | | 60 | | | | | |
| — | 1/4 | 30 | | | 0 | | | 98 | | | 100 | | | | | |
| 1/2 | 1/16 | 40 | 0 | S | 0 | 0 | — | 100 | 60 | S | 98 | 40 | S | | | |
| 1/2 | 1/8 | 65 | 0 | S | 0 | 0 | — | | 100 | | 60 | S | | | | |
| 1/2 | 1/4 | 90 | 30 | S | 10 | 0 | S | | | | | | | | | |
| 1 | 1/16 | 75 | 60 | S | 70 | 10 | S | 60 | 60 | Ad | 90 | 40 | S | | | |
| 1 | 1/8 | 85 | 60 | S | 60 | 10 | S | | | | 100 | 60 | S | | | |
| 1 | 1/4 | 100 | 72 | S | 50 | 10 | S | | | | | | | | | |
| 1/2 | — | 0 | | | 0 | | | 0 | | | 0 | | | | | |
| 1 | — | 10 | | | 0 | | | 0 | | | 0 | | | | | |
| 2 | — | 80 | | | 65 | | | 0 | | | 0 | | | | | |
| 4 | — | 99 | | | 75 | | | 0 | | | 0 | | | | | |
| — | 1/8 | 30 | | | 0 | | | 20 | | | 100 | | | | | |
| — | 1/4 | 95 | | | 0 | | | 40 | | | 90 | | | | | |
| — | 1/2 | 98 | | | 0 | | | 100 | | | 100 | | | | | |
| — | 1 | 100 | | | 0 | | | 100 | | | 100 | | | | | |
| — | 2 | 100 | | | 0 | | | 100 | | | 100 | | | | | |
| 1/2 | 1/4 | 78 | 95 | A | 0 | 0 | | 75 | 40 | S | 100 | 90 | S | | | |
| 1/2 | 1/2 | | | | 0 | 0 | | | | | | | | | | |
| 1/2 | 1 | | | | 0 | 0 | | | | | | | | | | |
| 1/2 | 2 | | | | 0 | 0 | | | | | | | | | | |
| 1 | 1/8 | 95 | 37 | S | 30 | 0 | S | 90 | 20 | S | | | | | | |
| 1 | 1/4 | 98 | 75 | S | 10 | 0 | S | 100 | 40 | S | 100 | 90 | S | | | |
| 1 | 1/2 | 100 | 95 | S | 30 | 0 | S | 90 | 100 | A | | | | | | |
| 1 | 1 | | | | 30 | 0 | S | | | | | | | | | |
| 1 | 2 | | | | 95 | 0 | S | | | | | | | | | |
| 2 | 1/8 | 98 | 86 | S | 80 | 65 | S | 85 | 20 | S | | | | | | |
| 2 | 1/4 | | | | 80 | 65 | S | 100 | 40 | S | | | | | | |
| 2 | 1/2 | | | | 70 | 65 | S | | | | | | | | | |
| 2 | 1 | | | | 100 | 65 | S | | | | | | | | | |
| 2 | 2 | | | | 98 | 65 | S | | | | | | | | | |

On watergrass, sesbania, and morning glory tests, both observed and expected results were too close to 100% for synergism evaluation, except as indicated. All curly dock tests produced 100% kill.

The compositions of the present invention are useful as herbicides in controlling the growth of undesirable vegetation by pre-emergence or post-emergence application to the locus where control is desired, including pre-plant and post-plant soil incorporation as well as surface application. The compositions are generally embodied in formulations suitable for convenient application. In general, such formulations will contain inert or occasionally active ingredients or diluent carriers in addition to the active compound. Examples of such ingredients or carriers are water, organic solvents, dust carriers, granular carriers, surface active agents, oil and water, water in oil emulsions, wetting agents, dispersing agents, and emulsifying agents. The herbicidal formulations generally take the form of dusts, wettable powders, granules, solutions, or emulsifiable concentrates.

Dusts are free-flowing powder compositions containing the herbicidal compound impregnated on a particulate carrier. The particle size of the carrier is usually in the range of from about 30 to 50 microns. Examples of suitable carriers are talc, bentonite, diatomaceous earth, and pyrophyllite. Anticaking and antistatic agents can be added, if desired. The composition generally contains up to 50% of active ingredient.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols; in which the alcohol groups are free, omega-substituted polyethylene glycols of relatively long chain length. A list of surface active agents suitable for use in agriculture formulations can be found in *Pesticide Formulations* by Wade Van Valkenburg, Marcel Dekker, Inc., N.Y., 1973 at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, and the like.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The formulations described above, employing phytotoxic or herbicidally effective amounts of the compositions described herein, are applied to the loci where control is desired in any conventional manner. The loci referred to above include soil, seeds, seedlings, and the actual plants, as well as flooded fields. Dusts and liquid compositions can be applied by the use of powder dusters, boom and hand sprayers and spray dusters. The compositions can also be applied from airplanes as dusts or sprays because they are effective in very low dosages. In order to modify or control growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvants or in combination with any of the above-described adjuvants. Other phytotoxic compounds useful in combination with the above-described compositions include, for example, 2,4-dichlorophenoxyacetic acids, 2,4,5-trichlorophenoxy acetic acid, 2-methyl-4-chlorophenoxyacetic acid, and the salts, esters and amides thereof; triazine derivatives, such as 2,4-bis (3-methoxypropylamino)-6-methyl-thio-s-triazine; 2-chloro-4-ethylamino-6-isopropylamino-s-triazine, and 2-ethylamino-4-isopropylamino-6-methylmercapto-s-triazine, urea derivatives such as 3-(3,4-dichlorophenyl)-1,1-dimethyl urea, and acetamides such as N,N-diallyl-α-chloroacetamide, N-(α-chloroacetyl) hexamethyleneimine, and N,N-diethyl-α-bromoacetamide, and the like; benzoic acids such as 3-amino-2,5-dichlorobenzoic; S-ethyl-dipropylthiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

The amount of a composition of the present invention which constitutes a phytotoxic or herbicidally effective amount depends upon the nature of the seeds or plants to be controlled. The rate of application of active ingredient varies from about 0.01 to about 50 pounds per acre, preferably about 0.1 to about 25 pounds per acre with the actual amount used depending on the overall cost and the desired results. It will be readily apparent to one skilled in the art that compositions exhibiting lower herbicidal activity will require a higher dosage rate for the same degree of control than more active compounds.

What is claimed is:

1. A synergistic herbicidal composition comprising a mixture of
(a) an anilide of the formula

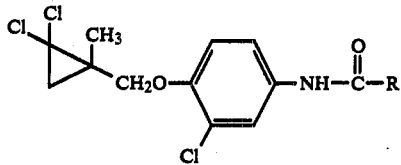

in which R is a member selected from the group consisting of $C_2$-$C_4$ alkenyl and cyclopropyl; and
(b) a thiocarbamate of the formula

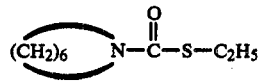

in a weight ratio of anilide to thiocarbamate of 0.01–10:1.

2. A composition according to claim 1 in which R is 1-methylvinyl.

3. A composition according to claim 1 in which R is cyclopropyl.

4. A composition according to claim 1 in which said weight ratio is 0.1–8:1.

5. A method of controlling undesirable vegetation which comprises applying to the locus where control is desired a synergistic herbicidal composition comprising a mixture of
(a) an anilide of the formula

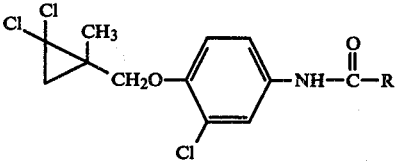

in which R is a member selected from the group consisting of $C_2$-$C_4$ alkenyl and cyclopropyl; and
(b) a thiocarbamate of the formula

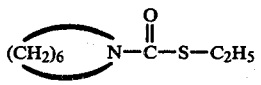

in a weight ratio of anilide to thiocarbamate of 0.01–10:1.

6. A method according to claim 5 in which R is 1-methylvinyl.

7. A method according to claim 5 in which R is cyclopropyl.

8. A method according to claim 5 in which said weight ratio is 0.1–8:1.

* * * * *